(12) United States Patent
Tsien et al.

(10) Patent No.: US 7,396,926 B2
(45) Date of Patent: Jul. 8, 2008

(54) BETA-LACTAMASE SUBSTRATES HAVING PHENOLIC ETHERS

(75) Inventors: Roger Y. Tsien, La Jolla, CA (US); Jianghong Rao, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/044,486

(22) Filed: Jan. 11, 2002

(65) Prior Publication Data

US 2003/0003526 A1    Jan. 2, 2003

Related U.S. Application Data

(60) Provisional application No. 60/261,313, filed on Jan. 12, 2001.

(51) Int. Cl.
| | |
|---|---|
| C07D 501/34 | (2006.01) |
| C07D 501/30 | (2006.01) |
| C07D 501/28 | (2006.01) |
| C07D 501/24 | (2006.01) |
| C07D 505/18 | (2006.01) |
| C07D 505/20 | (2006.01) |
| C07D 519/06 | (2006.01) |
| G01N 33/573 | (2006.01) |
| C07D 463/22 | (2006.01) |
| C07D 463/20 | (2006.01) |
| C07D 463/18 | (2006.01) |

(52) U.S. Cl. .................. 540/229; 540/215; 540/222; 540/227; 540/226; 540/301; 435/7.4; 435/173.2

(58) Field of Classification Search .............. 540/215, 540/222, 226, 227, 229, 301
See application file for complete search history.

(56) References Cited

U.S. PATENT DOCUMENTS 3,891,635 A * 6/1975 Henniger et al. ............ 540/228

(Continued)

FOREIGN PATENT DOCUMENTS

EP    0553741 A2    8/1993

OTHER PUBLICATIONS

Prasanna de Silva, A., et al. "Emerging fluorescence sensing technologies: From photophysical principles to cellular applications", *Proc. Natl. Acad. Sci USA* (1999) 96:8336-8337.

(Continued)

*Primary Examiner*—Mark L Berch
(74) *Attorney, Agent, or Firm*—Quine Intellectual Property Law Group; Gary Baker

(57) ABSTRACT

Provided are fluorescent substrates for β-lactamases having the general formula I:

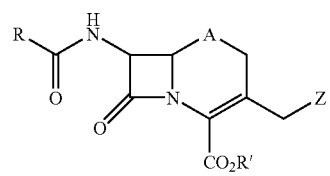

in which R is a benzyl, 2-thienylmethyl, or cyanomethyl group; R' is selected from the group consisting of H, physiologically acceptable salts or metal, ester groups, ammonium cations, —$CHR_2OCO(CH_2)_nCH_3$, —$CHR_2OCOC(CH_3)_3$, acylthiomethyl, acyloxy-alpha-benzyl, deltabutyrolactonyl, methoxycarbonyloxymethyl, phenyl, methylsulphinylmethyl, β-morpholinoethyl, dialkylaminoethyl, and dialkylaminocarbonyloxymethyl, in which $R_2$ is selected from the group consisting of H and lower alkyl; A is selected from the group consisting of S, O, SO, $SO_2$ and $CH_2$; and Z is a donor fluorescent moiety. Also provided are methods of use of the compound of general formula I.

2 Claims, 10 Drawing Sheets

The new substrate is synthetically easily accessible

U.S. PATENT DOCUMENTS

| | | | |
|---|---|---|---|
| 3,991,051 A * | 11/1976 | Breuer et al. | 540/222 |
| 4,110,534 A * | 8/1978 | Clark et al. | 540/215 |
| 4,113,591 A * | 9/1978 | Laundon et al. | 204/157.64 |
| 4,177,189 A * | 12/1979 | Akkerboom et al. | 540/308 |
| 5,338,843 A * | 8/1994 | Quante et al. | 540/222 |
| 5,741,657 A * | 4/1998 | Tsien et al. | 540/222 |
| 5,955,604 A * | 9/1999 | Tsien et al. | 540/222 |
| 6,031,094 A * | 2/2000 | Tsien et al. | 540/363 |
| 6,291,162 B1 * | 9/2001 | Tsien et al. | 435/6 |
| 2005/0227309 A1 * | 10/2005 | Corry et al. | 435/32 |
| 2005/0244907 A1 * | 11/2005 | Graham et al. | 435/8 |
| 2006/0014230 A1 * | 1/2006 | Murata | 435/18 |

OTHER PUBLICATIONS

Anderson Ellen G. et al. "Pre-Steady State β-Lactamase Kinetics", *The Journal of Biological Chemistry* (1981) 256(22): 11401-11404.

Zlokarnik, Gregor, et al. "Quantitation of Transcription and Clonal Selection of Single Living Cells with β-Lactamase as Reporter", *Science* (1998) 279(2):84-88.

Gao, Wenzhong, et al. "Novel Fluorogenic Substrates for Imaging β-Lactamase Gene Expression", *J. Am. Chem. Soc.* (2003) 125:11146-11147.

* cited by examiner cephalosporin-phenol ethers that we wish to claim:

Resorufin-cephalosporin cleaved by β-lactamase

BETA-LACTAMASE SUBSTRATES HAVING PHENOLIC ETHERS

RELATED APPLICATION DATA

This application claims priority under 35 U.S.C. § 119 to U.S. Provisional Application Ser. No. 60/261,313, filed Jan. 12, 2001 the contents of which is incorporated by reference in its entirety herein.

STATEMENT REGARDING FEDERALLY SPONSORED RESEARCH

This invention was made in part with government support under Grant No. NS27177 awarded by the National Institutes of Health. The government may have certain rights in the invention.

FIELD OF THE INVENTION

The present invention relates generally to the fields of chemistry and biology. More particularly, the present invention relates to compositions and methods for use in measuring gene expression.

BACKGROUND

A reporter gene assay measures the activity of a gene's promoter. It takes advantage of molecular biology techniques, which allow one to put heterologous genes under the control of any promoter and introduce the construct into the genome of a mammalian cell (Gorman, C. M. et al., Mol. Cell Biol. 2:1044-1051 (1982); Alam, J. and Cook, J. L., Anal. Biochem. 188:245-254, (1990)). Activation of the promoter induces the reporter gene as well as or instead of the endogenous gene. By design the reporter gene codes for a protein that can easily be detected and measured. Commonly it is an enzyme that converts a commercially available substrate into a product. This conversion is conveniently followed by either chromatography or direct optical measurement and allows for the quantification of the amount of enzyme produced.

Reporter genes are commercially available on a variety of plasmids for the study of gene regulation in a large variety of organisms (Alam and Cook, supra). Promoters of interest can be inserted into multiple cloning sites provided for this purpose in front of the reporter gene on the plasmid (Rosenthal, N., Methods Enzymol. 152:704-720 (1987); Shiau, A. and Smith, J. M., Gene 67:295-299 (1988)). Standard techniques are used to introduce these genes into a cell type or whole organism (e.g., as described in Sambrook, J., Fritsch, E. F. and Maniatis, T. Expression of cloned genes in cultured mammalian cells. In: Molecular Cloning, edited by Nolan, C. New York: Cold Spring Harbor Laboratory Press, 1989). Resistance markers provided on the plasmid can then be used to select for successfully transfected cells.

Ease of use and the large signal amplification make this technique increasingly popular in the study of gene regulation. Every step in the cascade DNA→RNA→Enzyme→Product→Signal amplifies the next one in the sequence. The further down in the cascade one measures, the more signal one obtains.

In an ideal reporter gene assay, the reporter gene under the control of the promoter of interest is transfected into cells, either transiently or stably. Receptor activation leads to a change in enzyme levels via transcriptional and translational events. The amount of enzyme present can be measured via its enzymatic action on a substrate. The substrate is a small uncharged molecule that, when added to the extracellular solution, can penetrate the plasma membrane to encounter the enzyme. A charged molecule can also be employed, but the charges need to be masked by groups that will be cleaved by endogenous cellular enzymes (e.g., esters cleaved by cytoplasmic esterases).

For a variety of reasons, the use of substrates which exhibit changes in their fluorescence spectra upon interaction with an enzyme are particularly desirable. In some assays, the fluorogenic substrate is converted to a fluorescent product. Alternatively, the fluorescent substrate changes fluorescence properties upon conversion at the reporter enzyme. The product should be very fluorescent to obtain maximal signal, and very polar, to stay trapped inside the cell.

To achieve the highest possible sensitivity in a reporter assay one has to maximize the amount of signal generated by a single reporter enzyme. An optimal enzyme will convert $10^5$ substrate molecules per second under saturating conditions (Stryer, L. Introduction to enzymes. In: Biochemistry, New York: W. H. Freeman and company, 1981, pp. 103-134). β-Lactamases will cleave about $10^3$ molecules of ideal substrates per second (Chang, Y. H. et al., Proc. Natl. Acad. Sci. USA 87:2823-2827 (1990)). Using a fluorogenic substrate one can obtain up to $10^6$ photons per fluorescent product produced, depending on the type of dye used, when exciting with light of the appropriate wavelength. The signal terminates with the bleaching of the fluorophore (Tsien, R. Y. and Waggoner, A. S. Fluorophores for confocal microscopy: Photophysics and photochemistry. In: Handbook of Biological Confocal Microscopy, edited by Pawley, J. B. Plenum Publishing Corporation, 1990, pp. 169-178). These numbers illustrate the theoretical magnitude of signal obtainable in this type of measurement. In practice a minute fraction of the photons generated will be detected, but this holds true for fluorescence, bioluminescence or chemiluminescence. A good fluorogenic substrate for a reporter enzyme has to have a high turnover at the enzyme in addition to good optical properties such as high extinction and high fluorescence quantum yield.

SUMMARY OF THE INVENTION

The novel β-lactamase substrates disclosed herein are easily synthesized. Prior β-lactamase substrates consist of a donor fluorophore and an acceptor chromophore connected by a cephalosporin. Fluorescence resonance energy transfer between the donor and acceptor is disrupted by β-lactamase cleavage of the cephalosporin. The novel substrates disclosed herein, are simpler phenolic ethers of cephalosporins in which β-lactamase attack releases the free phenolic chromophore, which is then detectable by fluorescence, chemiluminescence, or formation of colored precipitates. One advantage over prior substrates are that the novel molecules are smaller, can more readily give long-wavelength absorbencies or fluorescence and give lower detection limits.

In one embodiment, the present invention provides compounds that are substrates for β-lactamase that are suitable for use in a reporter gene assay. It is a further object of the invention to provide membrane-permeant compounds that can be transformed into substantially membrane-impermeant compounds after entry into a cell.

In accordance with the present invention, compounds are provided having general formula I:

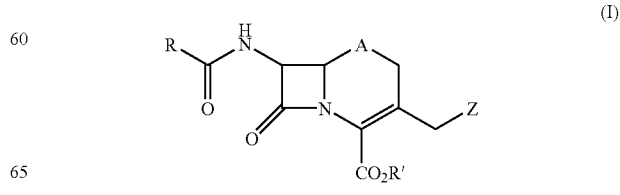

in which R is a benzyl, 2-thienylmethyl, or cyanomethyl group, or a quencher; R' is selected from the group consisting of H, physiologically acceptable salts or metal, ester groups, ammonium cations, —$CHR_2OCO(CH_2)_nCH_3$, —$CHR_2OCOC(CH_3)_3$, acylthiomethyl, acyloxy-alpha-benz, deltabutyrolactonyl, methoxycarbonyloxymethyl, phenyl, methylsulphinylmethyl, β-morpholinoethyl, dialkylaminoethyl, and dialkylaminocarbonyloxymethyl, in which $R_2$ is selected from the group consisting of H and lower alkyl; A is selected from the group consisting of S, O, SO, $SO_2$ and $CH_2$; and Z is a donor fluorescent moiety.

In another aspect, the present invention provides a method for determining whether a β-lactamase enzyme can cleave a compound of the present invention having the general formula I, or a membrane permeant derivative thereof. The method involves contacting a sample containing the enzyme with a compound of the present invention, exciting the sample with radiation of one or more wavelengths that are suitable for the cleaved compound, and determining the degree of fluorescence emitted from the sample. A degree of fluorescence emitted from the sample that is greater than an expected degree indicates that the βlactamase enzyme can cleave the compound and that the compound is a substrate for the β-lactamase enzyme.

In another aspect, the present invention provides methods for determining whether a sample contains β-lactamase activity. The method involves contacting the sample with a compound of the present invention having general formula I, exciting the sample with radiation of one or more wavelengths that are suitable for the cleaved compound, and determining the degree of fluorescence emitted from the sample. A degree of fluorescence emitted from the sample that is greater than an expected degree indicates the presence of β-lactamase activity in the sample. One aspect of this method is for determining the amount of an enzyme in a sample by determining the degree of fluorescence emitted at a first and second time after contacting the sample with a compound of the present invention. The difference in the degree of fluorescence emitted from the sample at the first and second time is determined. That difference reflects the amount of a β-lactamase enzyme in the sample.

In another aspect, the present invention is directed to screening assays using the compounds having general formula I of the present invention and a host cell, such as a mammalian cell, transfected with at least one recombinant nucleic acid molecule encoding at least one protein having β-lactamase activity. Such recombinant nucleic acid molecule comprise expression control sequences adapted for function in a eukaryotic cell, such as a vertebrate cell, operatively linked to a nucleotide sequence coding for the expression of a β-lactamase enzyme. The present invention also provides recombinant nucleic acid molecules comprising expression control sequences adapted for function in a eukaryotic cell, such as a vertebrate cell, operably linked to a nucleotide sequence coding for the expression of a cytosolic β-lactamase enzyme.

In another aspect, the present invention provides methods for determining the amount of β-lactamase activity in a cell. This method involves providing a sample comprising a host cell transfected with a recombinant nucleic acid molecule having an expression control sequences operatively linked to nucleic acid sequences coding for the expression of a β-lactamase enzyme. The sample can comprise whole host cells, or an extract of the host cells, which is contacted with a compound of the present invention. The amount of compound cleaved is measured, whereby the amount of substrate cleaved is related to the amount of β-lactamase activity in the host cell.

In another aspect, the present invention provides methods for monitoring the expression of a gene operably linked to a set of expression control sequences. The methods involve providing a host eukaryotic cell transfected with a recombinant nucleic acid molecule. The nucleic acid molecule comprises an expression control sequence operatively linked to nucleic acid sequences coding for the expression of a β-lactamase enzyme. If the host eukaryotic cell is a fungus, the β-lactamase is a cytosolic β-lactamase enzyme. A sample comprising the host eukaryotic cell, or an extract or conditioned medium produced therefrom or thereby, is contacted with a compound of the present invention. The amount of compound cleaved is determined using the methods of the present invention, wherein the amount of substrate cleaved is related to the amount of β-lactamase activity in the host eukaryotic cell, which is related to the expression of the gene.

In another aspect, the present invention provides methods for determining whether a test compound alters the expression of a gene operably linked to a set of expression control sequences. The methods involve providing a host eukaryotic cell transfected with a recombinant nucleic acid construct. The recombinant nucleic acid construct comprises a set of expression control sequences operably linked to nucleic acid sequences coding for the expression of a β-lactamase enzyme. The host eukaryotic cell is contacted with the test compound. This host eukaryotic cell is then contacted with a compound of the present invention. The amount of the compound of the present invention cleaved is then measured using the methods of the present invention, whereby the amount of the compound of the present invention cleaved is related to the amount of β-lactamase activity in the cell.

In another aspect, the present invention provides methods of clonal selection by providing cells transfected with a recombinant nucleic acid molecule comprising at least one expression control sequences operably linked to at least one nucleic acid sequence coding for the expression of a cytosolic β-lactamase enzyme. The cells are contacted with a substance that activates, inhibits, or has no effect on the activation of the expression control sequence. The cells are contacted with a compound of the present invention. The amount of the compound of the present invention cleaved is determined within individual cells (including each individual cell), whereby the amount of the compound of the present invention cleaved reflects the amount of β-lactamase activity in the cells. Cells having a selected level of β-lactamase activity are selected and propagated.

Another aspect of the present invention is to use a β-lactamase reporter gene and a compound of the present invention to screen test chemicals for biochemical. The method includes providing cells transfected with a recombinant nucleic acid molecule. The recombinant nucleic acid molecule comprises at least one expression control sequence operably linked to at least one nucleic acid sequence encoding for the expression of a β-lactamase enzyme. The cells are contacted with a test chemical that may activate, inhibit, or have no effect on the activation of the expression control sequence. The cells are contacted with a compound of the present invention and the amount of the compound cleaved is measured. The amount of compound cleaved reflects the amount of β-lactamase activity within the at least one cell, which reflects a biochemical activity within the at least one cell.

DETAILED DESCRIPTION OF THE INVENTION

Definitions

Figure 1:
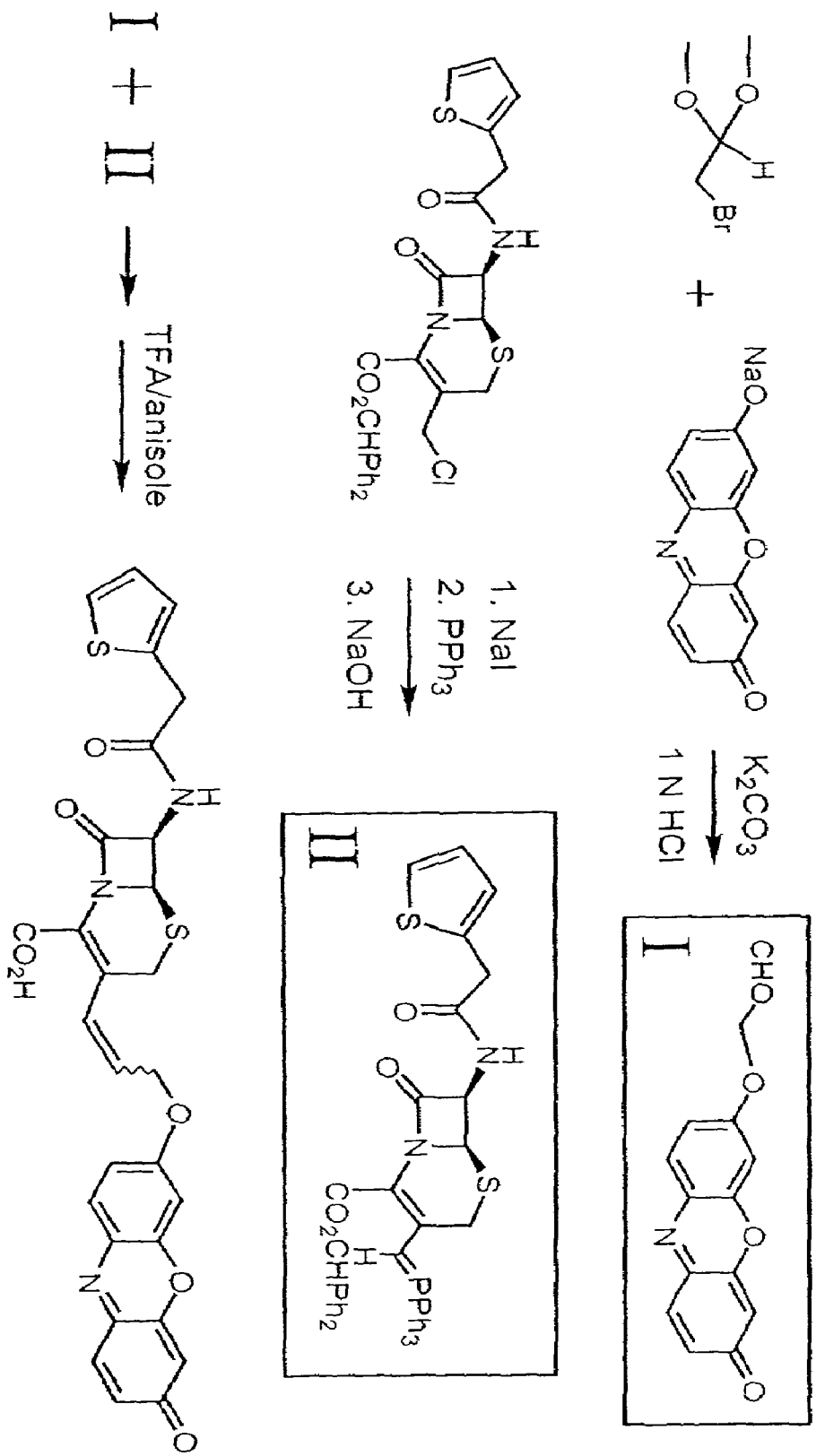
FIG. 1 shows the new substrate is synthetically easily accessible.
Figure 2:
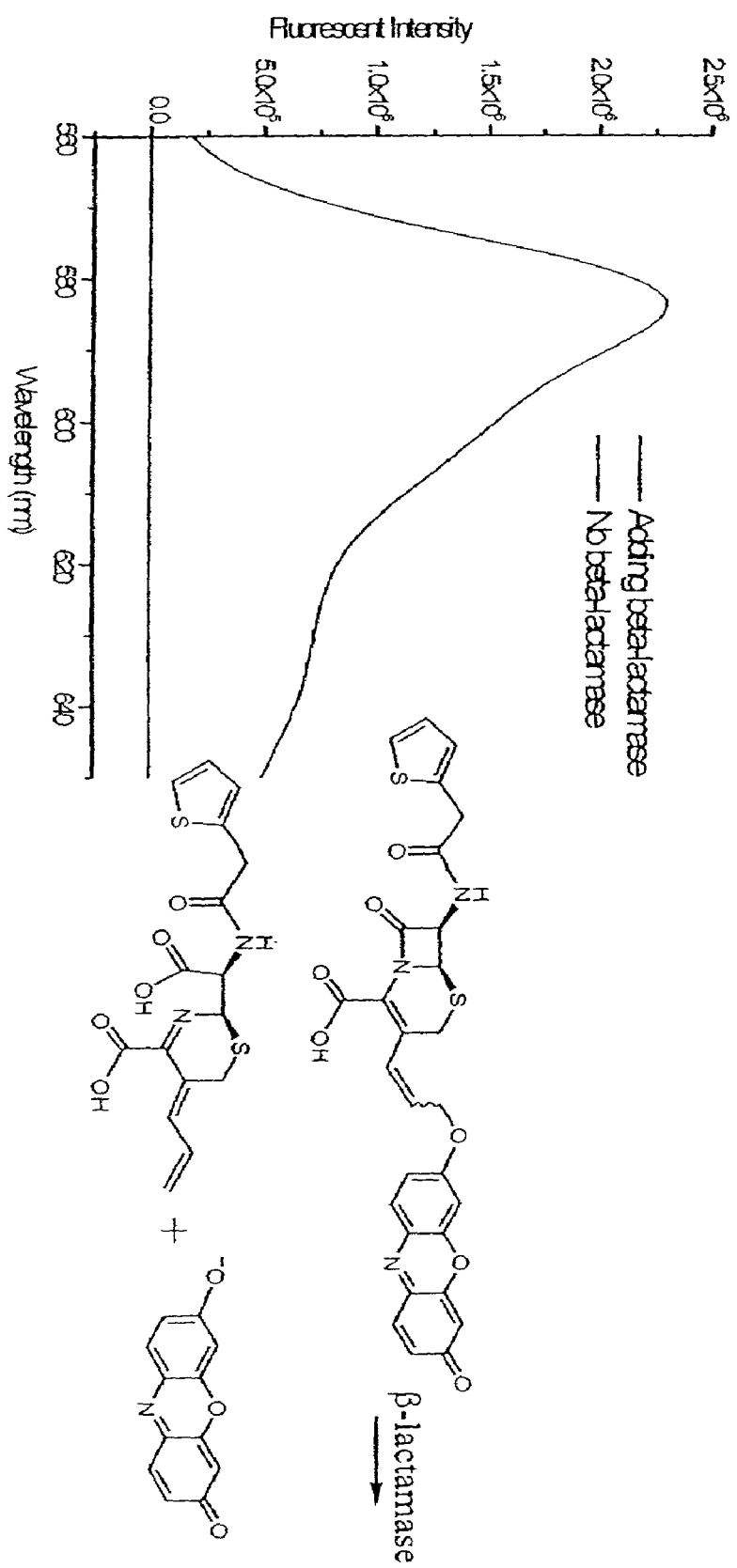
FIG. 2 shows enzymatic fragmentation can take place to the new substrate.
Figure 3:
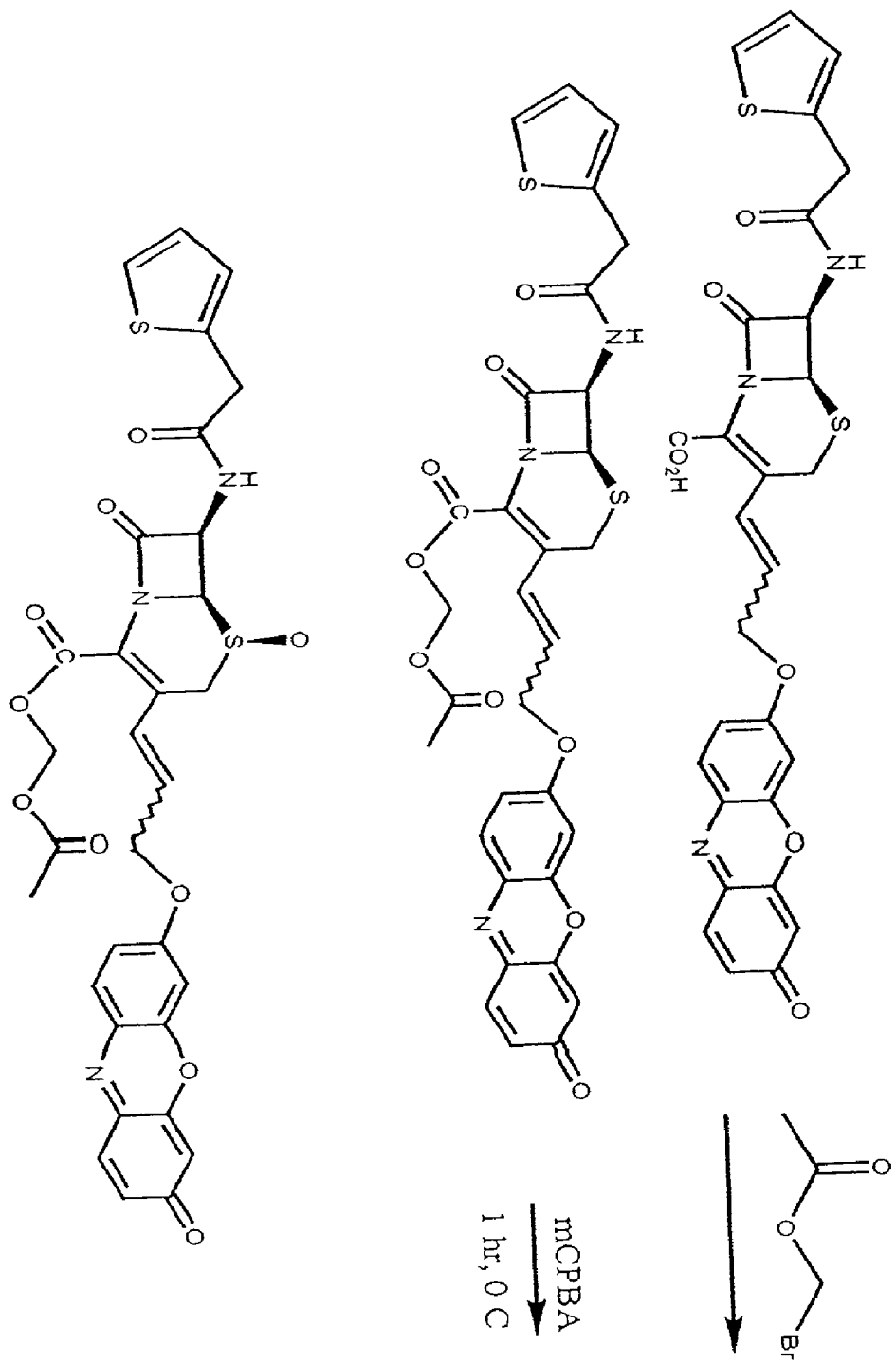
FIG. 3 shows synthesis of RECTO.
Figure 4:
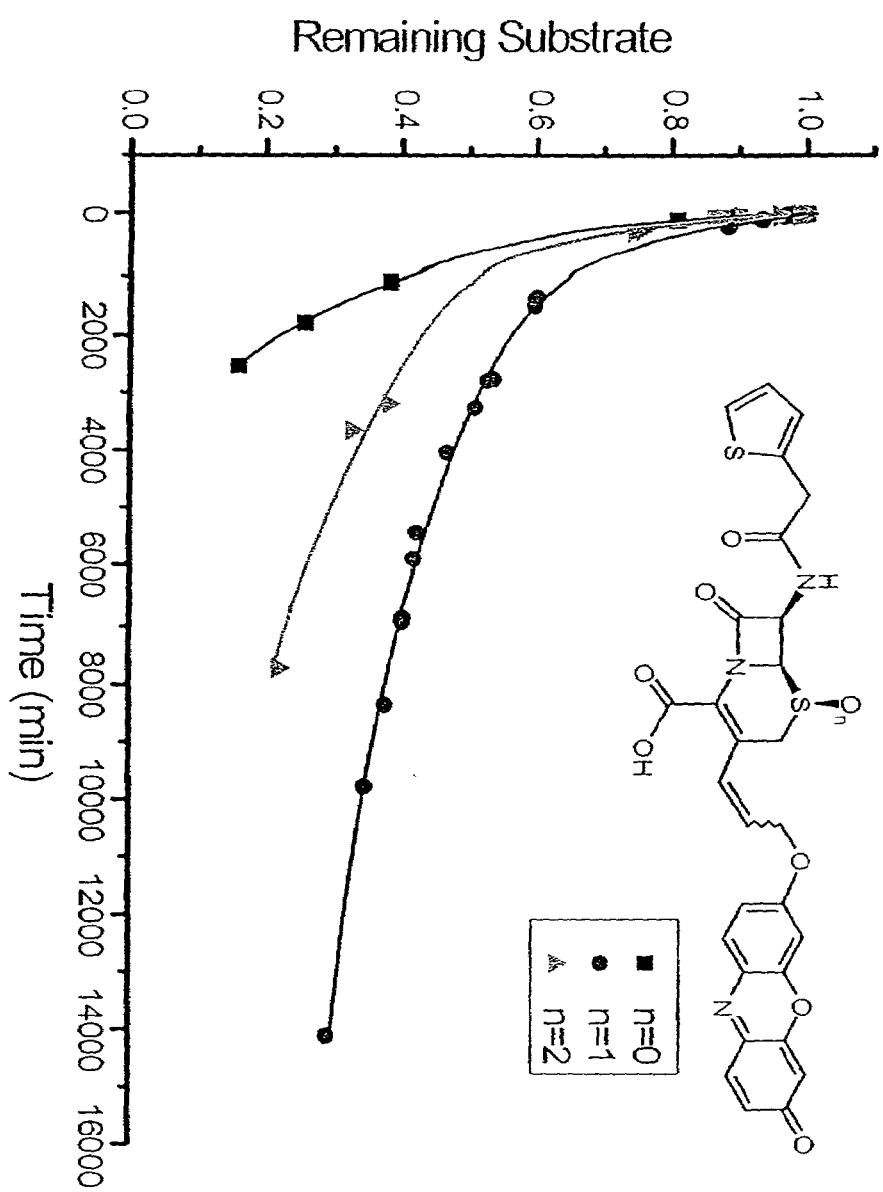
FIG. 4 shows oxidation state of the sulfide affects stability of the substrate.
Figure 5:
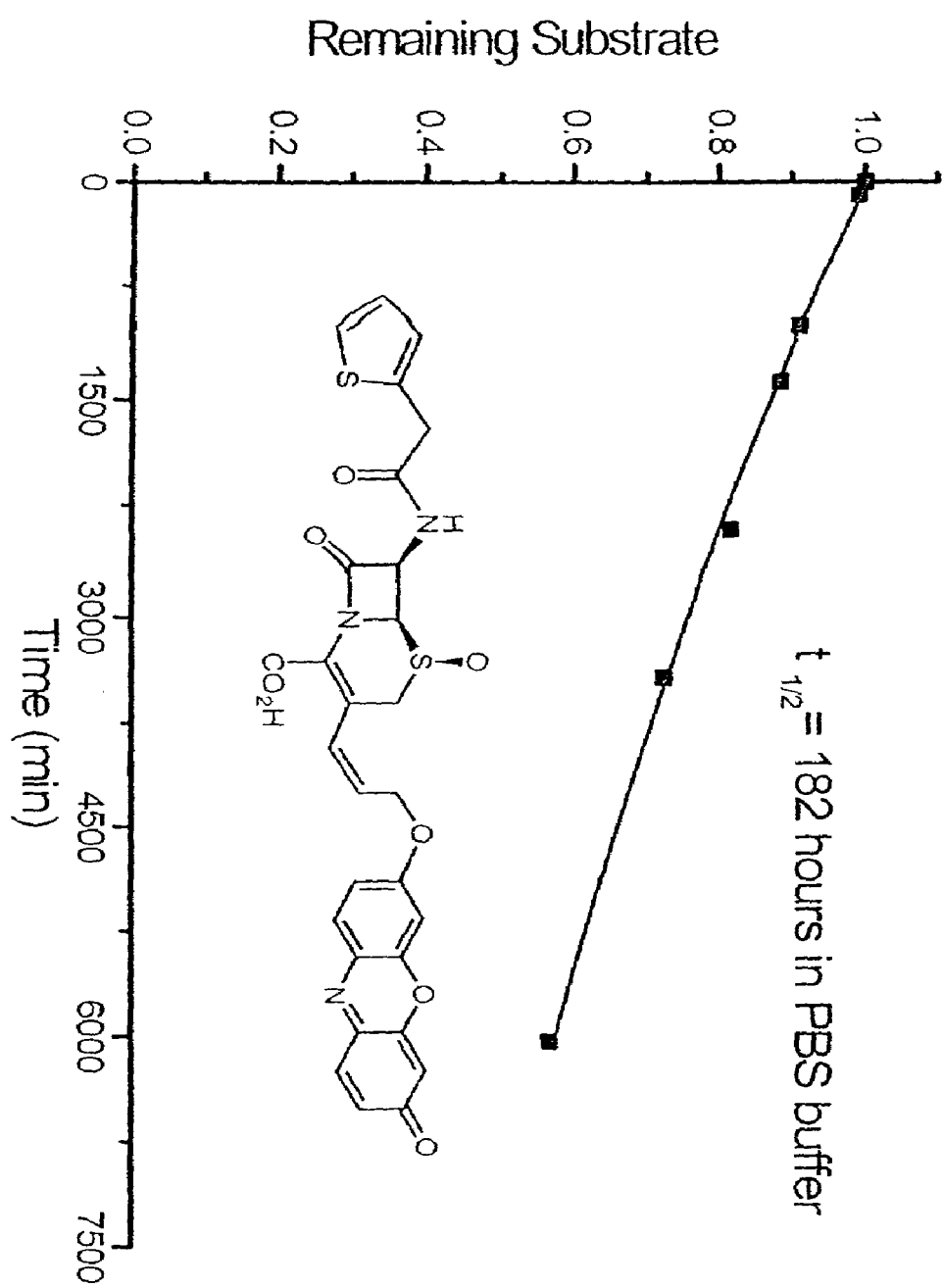
FIG. 5 shows sulfoxide increases substrate stability.
Figure 6:
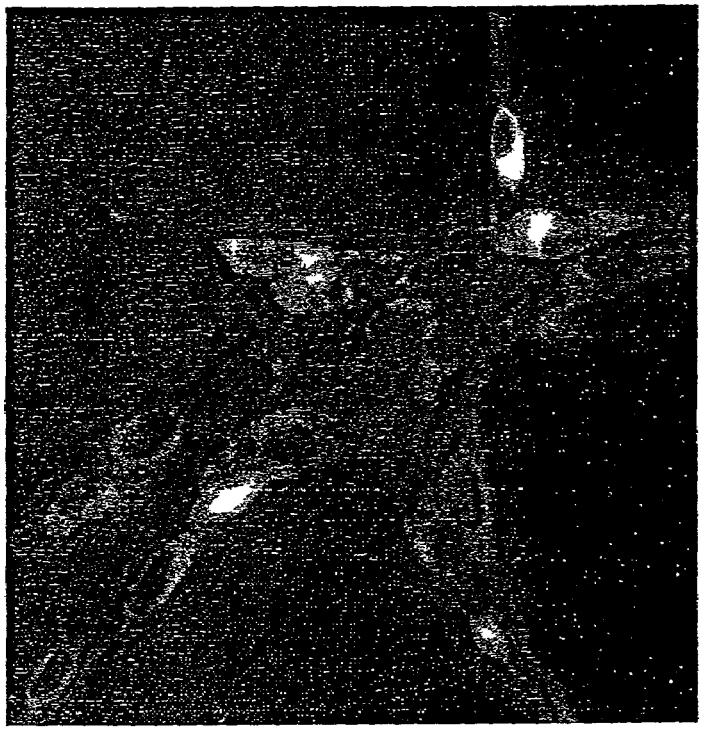
FIG. 6 shows increased resorufin deposition in β-lactamase-transfected vs. wild type cells.
Figure 6:
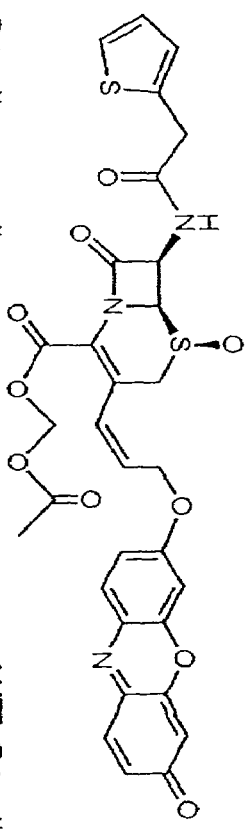
Figure 6:
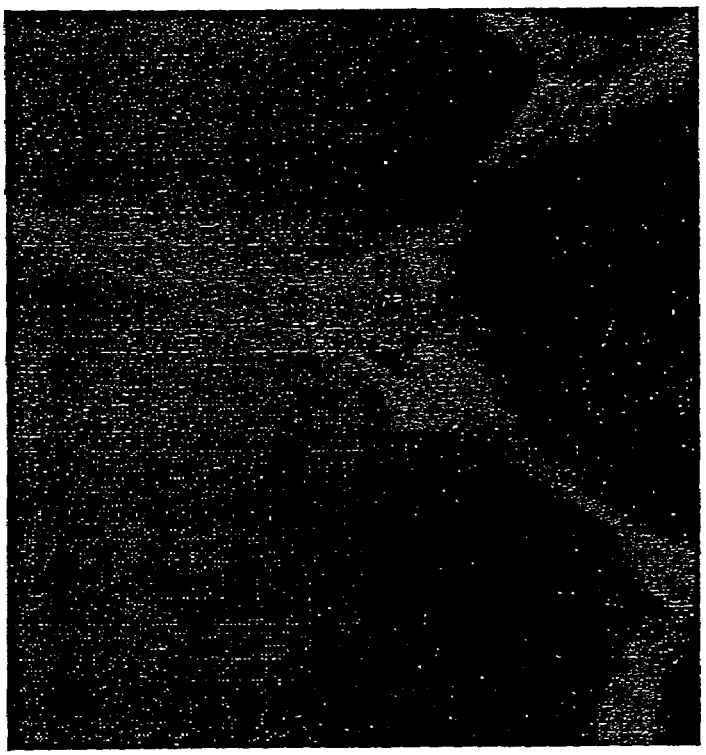
Figure 7:
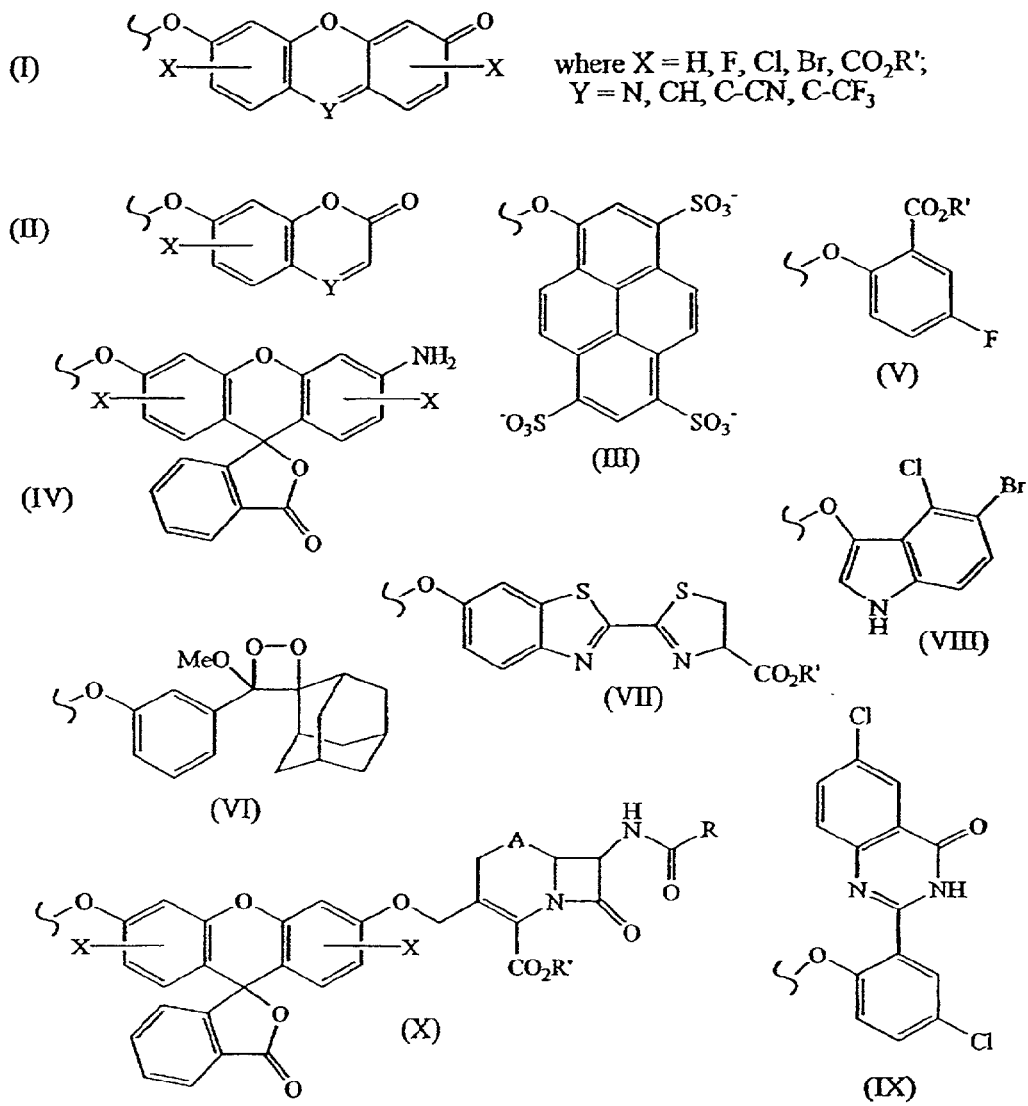
FIG. 7 shows cephalosporin-phenol.
Figure 8:
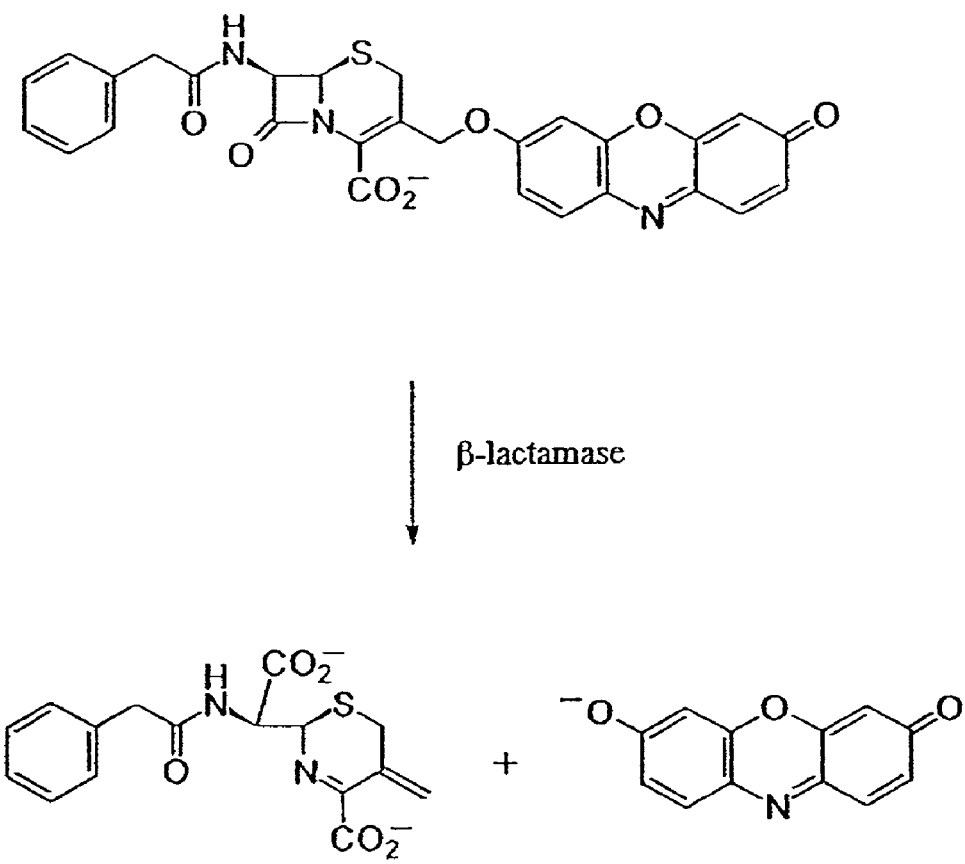
FIG. 8 shows resorufin-cephalosporin cleaved by β-lactamase.
Figure 9:
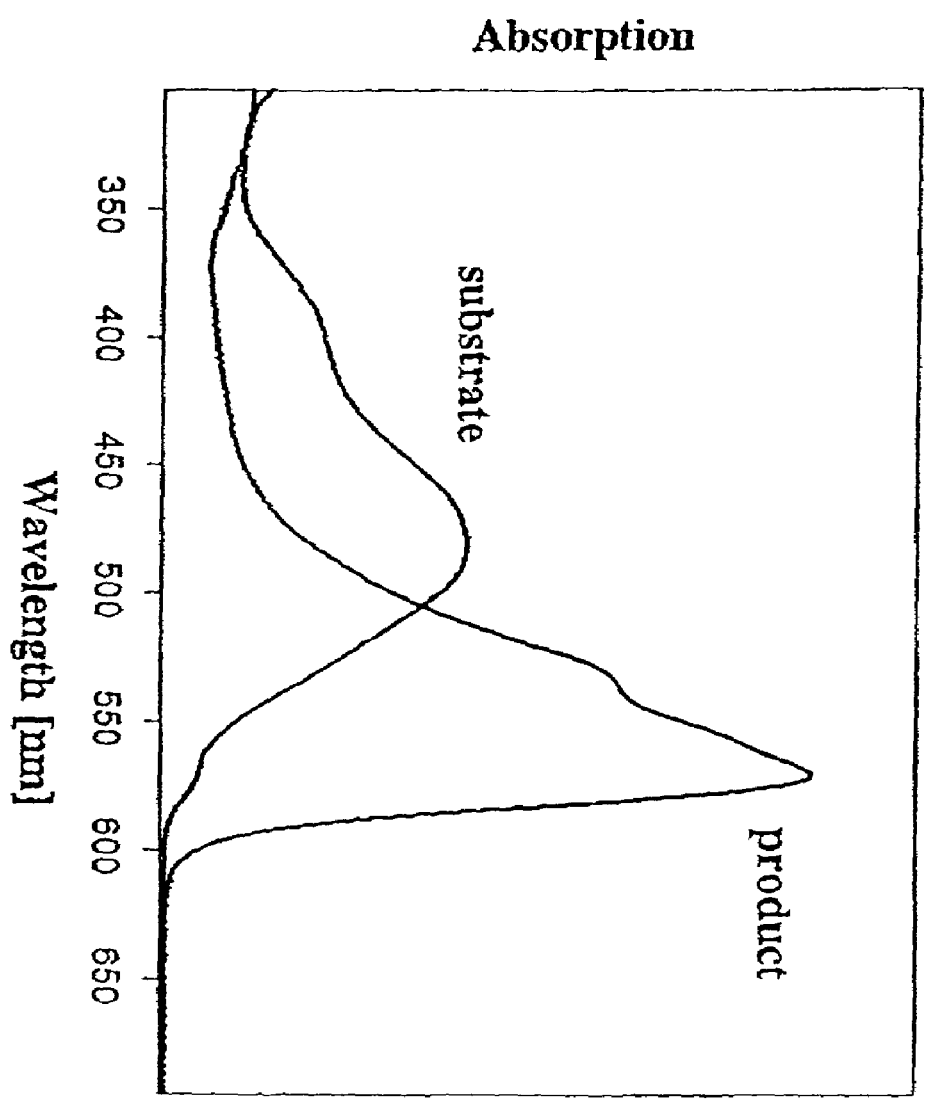
FIG. 9 shows absorption spectra of resorufin-cephalosporin before and after β-lactamase treatment.
Figure 10:
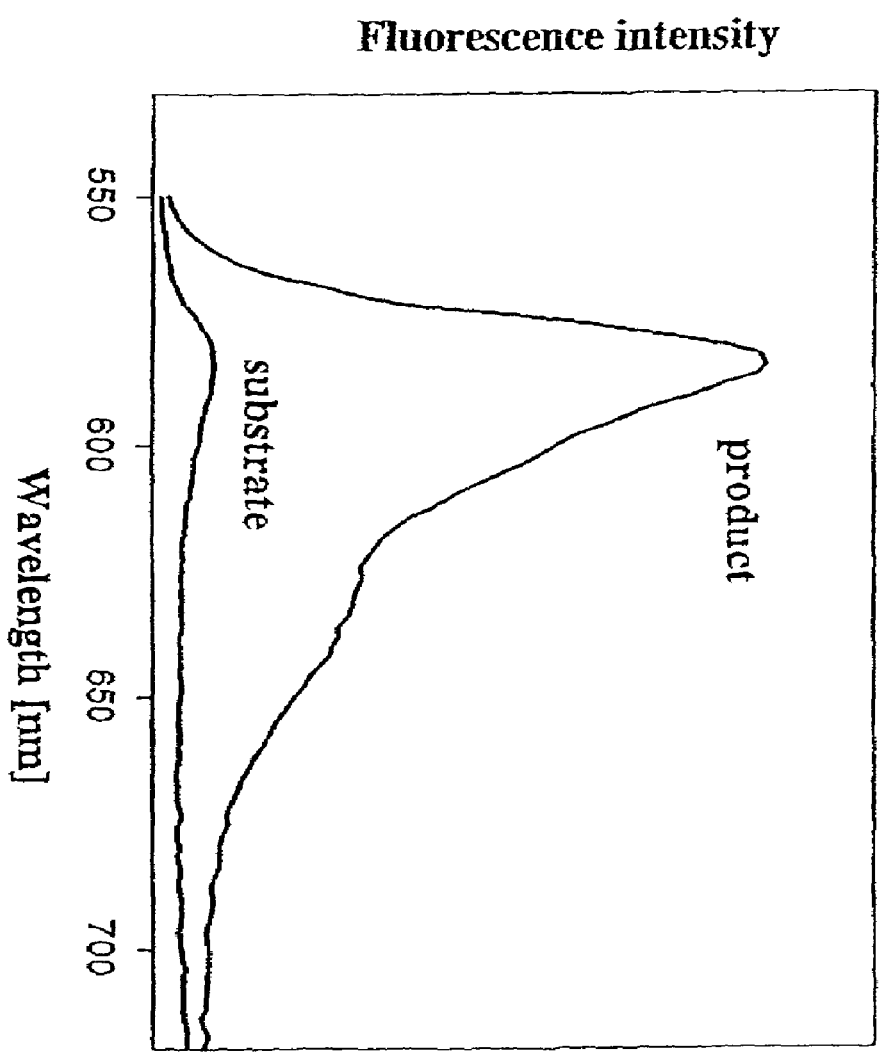
FIG. 10 shows fluorescence emission of resorufin-cephalosporin before and after β-lactamase treatment.

In accordance with the present invention and as used herein, the following terms are defined with the following meanings, unless stated otherwise.

The term "fluorescent donor moiety" refers the radical of a fluorogenic compound which can absorb energy and is capable of transferring the energy to another fluorogenic molecule or part of a compound. Suitable donor fluorogenic molecules include, but are not limited to, coumarins and related dyes; xanthene dyes such as fluoresceins, rhodols, and rhodamines; resorufins; cyanine dyes; bimanes; acridines; isoindoles; dansyl dyes; aminophthalic hydrazides such as luminol and isoluminol derivatives; aminophthalimides; aminonaphthalimides; aminobenzofurans; aminoquinolines; dicyanohydroquinones; and europium and terbium complexes and related compounds. Accordingly, a donor fluorescent moiety can be a dye or chromophore.

The term "quencher" refers to a chromophoric molecule or part of a compound which is capable of reducing the emission from a fluorescent donor when attached to the donor. Quenching may occur by any of several mechanisms including, for example, fluorescence resonance energy transfer, photoinduced electron transfer, paramagnetic enhancement of intersystem crossing, Dexter exchange coupling, and exciton coupling such as the formation of dark complexes. The term "acceptor" as used herein refers to a quencher which operates via fluorescence resonance energy transfer. Many acceptors can reemit the transferred energy as fluorescence. Examples include coumarins and related fluorophores, xanthenes such as fluoresceins, rhodols and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, di- and triphenylmethanes.

The term "dye" refers to a molecule or part of a compound which absorbs specific frequencies of light, including, but not limited to, ultraviolet light. The terms "dye" and "chromophore" are used herein synonymously.

The term "fluorophore" refers to chromophore or dye which fluoresces.

The term "membrane-permeant derivative" means a chemical derivative of a compound of general formula I containing at least one acylated aromatic hydroxyl, acylated amine, or alkylated aromatic. hydroxyl wherein the acyl group contains 1 to 5 carbon atoms and wherein the alkyl group is selected from the group consisting of —CH$_2$OC(O) alk, —CH$_2$SC(O)alk, —CH$_2$OC(O)Oalk, lower acyloxy-alpha-benzyl, and deltabutyrolactonyl; wherein alk is lower alkyl of 1 to 4 carbon atoms. These derivatives are better able to cross cell membranes, i.e. membrane permeant, because hydrophilic groups are masked to provide more hydrophobic derivatives. Also, the masking groups are designed to be cleaved from the fluorogenic substrate within the cell to generate the derived substrate intracellularly. Because the substrate is more hydrophilic than the membrane permeant derivative it is now trapped within the cells.

The term "alkyl" refers to straight, branched, and cyclic aliphatic groups of 1 to 8 carbon atoms, preferably 1 to 6 carbon atoms, and most preferably 1 to 4 carbon atoms. The term "lower alkyl" refers to straight and branched chain alkyl groups of 1 to 4 carbon atoms.

The term "aliphatic" refers to saturated and unsaturated alkyl groups of 1 to 10 carbon atoms, preferably 1 to 6 carbon atoms, and most preferably 1 to 4 carbon atoms.

The term "β-lactamase" refers to an enzyme that can cleave a β-lactam ring. Examples of a β-lactamase enzyme include the naturally occurring forms of β-lactamase and enzymes that have been prepared by mutagenesis of β-lactamase enzymes. If a β-lactamase enzyme can cleave the β-lactam ring in particular compound having the general formula I (or its membrane permeant derivative), then this particular compound is a substrate of this invention for this particular β-lactamase enzyme (see, for example, WO 96/30540, published Oct. 3, 1996).

β-Lactamases are excellent enzymes due to their diffusion-controlled catalysis of β-lactam hydrolysis (Christensen, H. et al., Biochem. J. 266:853-861 (1990)). Upon examination of the other properties of this class of enzymes, it was determined that they were suited to the task of an intracellular reporter enzyme. They cleave the β-lactam ring of β-lactam antibiotics, such as penicillins and cephalosporins, generating new charged moieties in the process (O'Callaghan, C. H. et al., Antimicrob. Agents. Chemother. 8:57-63, (1968); Stratton, C. W., J. Antimicrob. Chemother. 22, Suppl. A: 23-35 (1988)). A first generation cephalosporin is illustrated below, 1, with the arrow pointing to the site of cleavage by β-lactamase. The free amino group thus generated 2 donates electron density through the vinyl group to promote irreversible cleavage of a nucleofugal group R$_2$ from the 3'-position. R$_2$ is thus free to diffuse away from the R$_1$-cephalosporin conjugate 3.

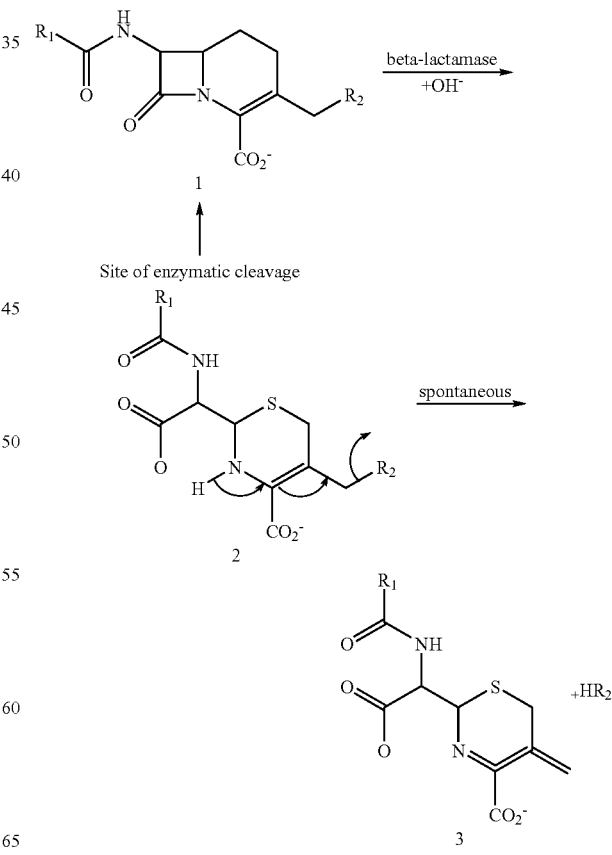

β-Lactamases are a class of enzymes that have been very well characterized due to their clinical relevance in making bacteria resistant to β-lactam antibiotics (Waley, S. G., Sci. Prog. 72:579-597 (1988); Richmond, M. H. et al., Ann. N.Y. Acad. Sci. 182:243-257 (1971)). Most β-lactamases have been cloned and their amino acid sequence determined (see, e.g., Ambler, R. P., Phil. Trans. R. Soc. Lond. Ser. B. 289: 321-331 (1980)).

A gene encoding β-lactamase is known to molecular biologists as the ampicillin resistance gene (Amp$^r$) and is commonly used to select for successfully transduced bacteria (Castagnoli, L. et al., Genet.Res. 40: 217-231 (1982)); clones thereof are almost universally available. The enzyme catalyzes the hydrolysis of a β-lactam ring and will not accept peptides or protein substrates (Pratt, R. F. and Govardhan, C. P., Proc. Natl. Acad. Sci. USA 81:1302-1306 (1984); Murphy, B. P. and Pratt, R. F., Biochemistry 30:3640-3649 (1991)). The kinetics of this reaction is well understood and there is no product inhibition (Bush, K. and Sykes, R. B., Antimicrob. Agents. Chemother. 30:6-10 (1986); Christensen et al. (1990), supra). The enzyme substrates are less polar than the products.

The carboxyl group in the substrate can be easily masked by an acetoxymethyl ester (Jansen, A. B. A. and Russell, T. J., J. Chem. Soc. 2127-2132, (1965); Daehne, W. et al., J. Med. Chem. 13:607-612 (1970)), which is readily cleaved by endogenous mammalian intracellular esterases. Conversion by these esterases followed by cleavage of the β-lactam by β-lactamase generates two negative charges and a tertiary amine. Multiple chromogenic substrates of different design have been reported and are commercially available (Jones, R. N. et al., J. Clin. Microbiol. 15:677-683 (1982); Jones, R. N. et al., J. Clin. Microbiol. 15:954-958 (1982); O'Callaghan, C. H. et al., Antimicrob. Agents. Chemother. 1:283-288 (1972)).

A large number of β-lactamases have been isolated and characterized, all of which would be suitable for use in accordance with the present invention. Initially, β-lactamases were divided into different classes (I through V) on the basis of their substrate and inhibitor profiles and their molecular weight (Richmond, M. H. and Sykes, R. B., Adv. Microb. Physiol. 9:31-88 (1973)). More recently, a classification system based on amino acid and nucleotide sequence has been introduced (Ambler, R. P., Phil. Trans. R. Soc. Lond. Ser. B. 289:321-331 (1980)). Class A β-lactamases possess a serine in the active site and have an approximate weight of 29 kd. This class contains the plasmid-mediated TEM β-lactamases such as the RTEM enzyme of pBR322. Class B β-lactamases have an active-site zinc bound to a cysteine residue. Class C enzymes have an active site serine and a molecular weight of approximately 39 kd, but have no amino acid homology to the class A enzymes.

The coding region of an exemplary β-lactamase which may be employed in the present invention is described in U.S. Pat. No. 5,955,604. The pTG2dell containing this sequence has been described (Kadonaga, J. T. et al., J. Biol. Chem. 259: 2149-2154 (1984)). The entire coding sequence of wild-type pBR322 β-lactamase has also been published (Sutcliffe, J. G., Proc. Natl. Acad. Sci. USA 75:3737-3741 (1978)). As would be readily apparent to those skilled in the field, this and other comparable sequences for peptides having β-lactamase activity would be equally suitable for use in accordance with the present invention. The β-lactamase reporter gene is employed in an assay system in a manner well known per se for the use of reporter genes (for example, in the form of a suitable plasmid vector).

In conjunction with a suitable β-lactamase, there are employed in accordance with the present invention fluorogenic substrates of the general formula I or formula IA:

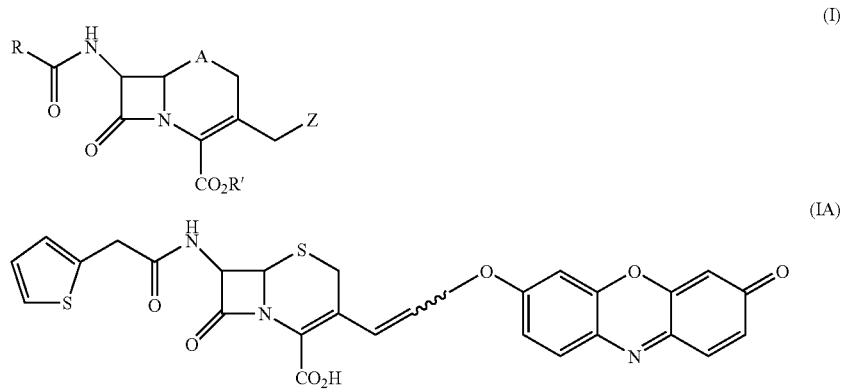

in which R is a benzyl, 2-thienylmethyl, or cyanomethyl group; R' is selected from the group consisting of H, physiologically acceptable salts or metal, ester groups, ammonium cations, —CHR$_2$OCO(CH$_2$)$_n$CH$_3$, —CHR$_2$OCOC(CH$_3$)$_3$, thioacetyl alpha-acyloxy-benzyl, deltabutyrolactonyl, methoxycarbonyloxymethyl, phenyl, methylsulphinylmethyl, β-morpholinoethyl, dialkylaminoethyl, and dialkylaminocarbonyloxymethyl, in which R$_2$ is selected from the group consisting of H and lower alkyl; A is selected from the group consisting of S, O, SO, SO$_2$ and CH$_2$; and Z is a donor fluorescent moiety, selected from the group consisting of:

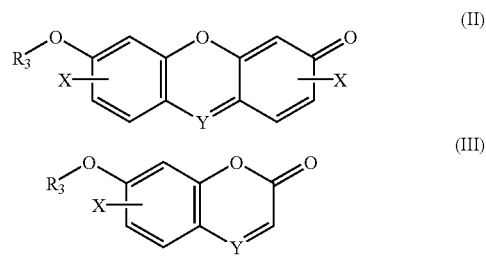

R₃ is a linker for the fluorescent donor. The linker R₃ serves the purpose of attaching the fluorescent donor to the cephalosporin phenol ether derived backbone. Suitable linkers for use as R₃ include, but are not limited to, a direct bond to a heteroatom (e.g., O, N or S) in the dye's chromophore or the following: —O(CH₂)ₙ—, —S(CH₂)ₙ—, —NR₂(CH₂)ₙ—, —N₊R₂ (CH₂)ₙ, —OCONR₂(CH₂)ₙ—, —O₂C(CH₂)ₙ—, —SCSNR₂(CH₂)ₙ—, —SCSO(CH₂)ₙ—, —S(CH₂)ₙCONR₂(CH₂)ₘ, —S(CH₂)ₙNR₂CO(CH₂)ₘ, and in which $R_2$, n and m are as previously defined; and m is an integer from 0 to 4. Particularly preferred groups are —S(CH₂)ₙ. Also preferred is H. In a one aspect, the compounds of the present invention are membrane-permeant.

As would readily be appreciated by those skilled in the art, the efficiency of fluorescence resonance energy transfer depends on the fluorescence quantum yield of the donor fluorophore, the donor-acceptor distance and the overlap integral of donor fluorescence emission and acceptor absorption. The energy transfer is most efficient when a donor fluorophore with high fluorescence quantum yield (preferably, one approaching 100%) is paired with an acceptor with a large. extinction coefficient at wavelengths coinciding with the emission of the donor. The dependence of fluorescence energy transfer on the above parameters has been reported (Forster, T. (1948) Ann. Physik 2:55-75; Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, Vol 30, ed. Taylor, D. L. & Wang, Y.-L., San Diego: Academic Press (1989), pp. 219-243; Turro, N. J., Modern Molecular Photochemistry, Menlo Part: Benjamin/Cummings Publishing Co., Inc. (1978), pp. 296-361), and tables of spectral overlap integrals are readily available to those working in the field (for example, Berlman, I. B. Energy transfer parameters of aromatic compounds, Academic Press, New York and London (1973)). The distance between donor fluorophore and acceptor dye at which fluorescence resonance energy transfer (FRET) occurs with 50% efficiency is termed $R_0$ and can be calculated from the spectral overlap integrals. For the donor-acceptor pair fluorescein tetramethyl rhodamine which is frequently used for distance measurement in proteins, this distance $R_0$ is around 50-70Å (dos Remedios, C. G. et al. (1987) J. Muscle Research and Cell Motility 8:97-117). The distance at which the energy transfer in this pair exceeds 90% is about 45Å. When attached to the cephalosporin backbone the distances between donors and acceptors are in the range of 10Å to 20Å, depending on the linkers used and the size of the chromophores. For a distance of 20Å, a chromophore pair will have to have a calculated $R_0$ of larger than 30Å for 90% of the donors to transfer their energy to the acceptor, resulting. in better than 90% quenching of the donor fluorescence. Cleavage of such a cephalosporin by β-lactamase relieves quenching and produces an increase in donor fluorescence efficiency in excess of tenfold. Accordingly, it is apparent that identification of appropriate donor-acceptor pairs for use as taught herein in accordance with the present invention would be essentially routine to one skilled in the art.

To measure β-lactamase activity in the cytoplasm of living cells,. smaller molecular weight chromophores as hereinafter described are in general preferred over larger ones as substrate delivery becomes a problem for larger compounds. Large molecules, especially those over about 1200 daltons, also tend to bind more avidly to cellular constituents than small ones, thereby removing at least some of them from access and cleavage by. β-lactamase.

Suitable chromaphores are disclosed in U.S. Pat. No. 5,955,604, the disclosure of which is incorporated herein by reference in its entirety.

A general method for synthesis of compounds of formula IA is depicted below (Scheme 1). As one of ordinary skill in the art will appreciate, the methods below can be used for a variety of derivatives, and other methods of synthesis are possible, including synthetic methods for preparing the compounds of general formula I.

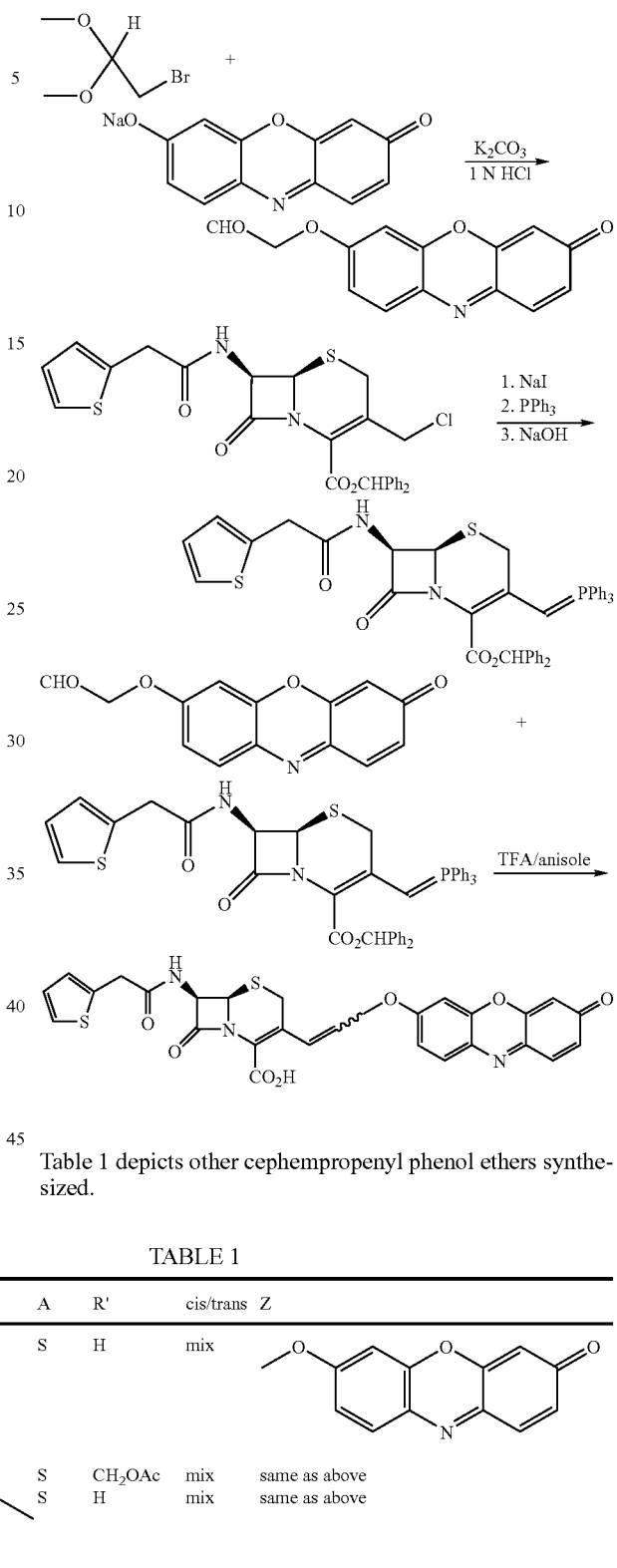

Table 1 depicts other cephempropenyl phenol ethers synthesized.

TABLE 1

| Compound | R | A | R' | cis/trans | Z |
|---|---|---|---|---|---|
| 1 | CH₃ | S | H | mix | ![structure] |
| 2 | CH₃ | S | CH₂OAc | mix | same as above |
| 3 | ![thiophene-CH₂] | S | H | mix | same as above |
| 4 | same | S | CH₂OAc | mix | same as above |
| 5 | same | SO | H | cis | same as above |
| 6 | same | SO | H | trans | same as above |
| 7 | same | SO | CH₂OAc | mix | same as above |
| 8 | same | SO₂ | H | mix | same as above |

TABLE 1-continued

| Compound | R | A | R' | cis/trans | Z |
|---|---|---|---|---|---|
| 9 | same | SO$_2$ | CH$_2$OAc | mix | same as above |
| 10 | same | SO | CHPh$_2$ | mix | 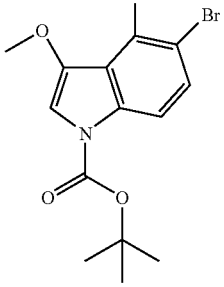 |

The cephalosporin starting materials are commercially available cephalosporin derivatives 7-aminocephalosporanic acid or 7-amino 3'-chlorocephalosporanic acid as its benzhydryl or tertiary butyl ester (R$_0$).

A large variety of phenolic fluorophores could be substituted for the resorufin derivative disclosed herein. Examples include the courmarin, the pyrene, and the rhodol. In each case the fluorescence is greatly enhanced and shifts to longer wavelengths when the free phenolic group is release from the ether linkage to the cephalosporin.

Another variety of fluorophore formation is exemplified by the fluorosalicylate ether. Once the free fluorosalicylate is released it forms a mixed chelate with terbium-EDTA or europium-EDTA, which would be provided as an additional component of the assay system. Excitation of the fluorosalicylate causes energy transfer to the lanthanide ion, which then emits with extremely sharp peaks and millisecond-long fluorescence lifetimes. Both the latter properties make this fluorescence very distinctive and easy to separate from autofluorescence backgrounds.

A chemiluminescence readout can also be generated by use of the adamantylidene-dioxetane. The release of the free phenol triggers spontaneous fragmentation of the dioxetane and emission of light. Another version is the luciferin ether. In this case ATP is added and luciferase to get the light output. Only free luciferin, not a luciferin derivative is a substrate for the enzyme. The advantage over the adamanylidene-dioxetane would be the much higher quantum efficiency of the luciferase-catalyzed chemiluminescence compared to the non-enzymatic glow.

Colored or fluorescent precipitates should result from the indolyl or 2-(2-hydroxyphenyl) quinazolin-4-one substrates. Release of the free phenol triggers oxidation of 3-hydroxyindoles to blue indigo precipitates. The free 2-(2-hydroxyphenyl) quinazolin-4-one likewise forms a brightly fluorescent precipitate.

It is also possible to couple two cephalosporins to a bis (phenol) such as the fluorescein. Only when both phenols are freed does the fluorescein become fully fluorescent.

The cephalosporin backbone serves as a cleavable linker. After cleavage it provides the charges necessary to keep a dye inside the cell. Dyes may be chosen in a manner that one dye absorbs light (quencher or acceptor chromophore) at the wavelength that the other one emits (donor fluorophore). In the intact cephalosporin the two dyes are in close proximity to each other. When exciting the donor fluorophore one observes fluorescence resonance energy transfer (FRET) from the donor to the acceptor instead of donor fluorescence (Forster, T., Ann. Physik 2:55-75 (1948)). If the acceptor is a nonfluorescent dye the energy is given off to the solvent; the donor fluorescence is quenched. In the case of the acceptor being itself a fluorescent dye, fluorescence re-emission occurs at the acceptor's emission wavelength. In polar solvents such as water, hydrophobic donor and acceptor fluorophores can stack when separated by a short flexible linker. Due to this association in the ground state, a dark complex is formed (Yaron, A. et al., Anal. Biochem. 95: 228-235 (1979)). In this complex, neither fluorophore can emit light, causing the fluorescence of both dyes to be quenched (Bojarski, C. and Sienicki, K. Energy transfer and migration in fluorescent solutions. In: Photochemistzy and Photophysics, edited by Rabek, J. F. Boca Raton: CRC Press, Inc., 1990, pp. 1-57). In either case, a large change in fluorescence goes along with β-lactam cleavage, which can be used to measure β-lactamase activity. As both dyes diffuse away from each other, stacking and energy transfer are disrupted. Cephalosporins carrying a donor and an acceptor dye which fluoresces are referred to herein as FRET-cephalosporins.

Fluorescence resonance energy transfer has been used as a spectroscopic ruler for measuring molecular distances in proteins and peptides as it is effective in the range from 10-100 angstroms. This energy transfer is proportional to the inverse sixth power of the distance between donor and acceptor. Its efficiency is higher, the better donor emission and acceptor absorbance overlap, and the longer the fluorescence lifetime of the donor (in absence of the acceptor). FRET can be very efficient over distances of 10-20 angstroms.

In the cephalosporin, distances for attachment of donor and acceptor are greater than 10 angstroms and a minimum of 10 bond-lengths, if one includes the two minimal spacers at 7- and 3-positions. Over this distance FRET is very efficient, if the right donor-acceptor pairs are chosen. Upon cleavage, fluorescence increases due to loss of the quencher dye.

The fluorogenic substrates of the invention are initially colorless and nonfluorescent outside cells. The substrates are designed so they readily cross cell membranes into the cytoplasm, where they are converted to fluorescent compounds by endogenous nonspecific esterases and stay trapped due to their charges. In the intact molecules, fluorescence energy transfer occurs leading to fluorescence at a particular wavelength when the substrates are excited. Lactamase cleavage of the β-lactam ring is followed by expulsion of the fluorescein moiety with loss of fluorescence energy transfer. Excitation of the modified substrate now results in fluorescence at a different wavelength or results in an increase in detected fluorescence.

The assay systems of the present invention further provide an advantageous and rapid method of isolation and clonal selection of stably transfected cell lines containing reporter genes and having the desired properties which the transfection was intended to confer, e.g. fluorescent signal response after activation of a transfected receptor with a high signal-to-noise ratio from a high proportion of isolated cells. Current procedures for clonal selection of satisfactorily transfected, genetically engineered cells from the initial population, are done mainly by replica plating of colonies, testing of one set of colonies, visual selection of preferred clones, manual isolation of the replicas of the preferred clones by pipetting, and prolonged cellular cultivations. This procedure is laborious and time-consuming; it may require several months to generate a clone useful for assays suited to drug screening. Moreover, it is difficult to manually select and maintain more than a few hundred clones. Using the assays of this present invention, the desired signal from cellular β-lactamase reporter system can be maintained within living and viable cells. Replica plating of colonies is unnecessary because single cells can be assayed and remain viable for further multiplication. Thus, from the population of initially transfected cells, one can rapidly select those few individual living cells with the best fluorescent signal, using automated instruments such as a fluorescent-activated cell sorter, e.g. the Becton Dickinson FACS Vantage™. The selected cells are then collected for cultivation and propagation to produce a clonal cell line with the desired properties for assays and drug screening.

As would be immediately apparent to those working in the field, the combination of a novel substrate in accordance with the invention and a suitable β-lactamase may be employed in a wide variety of different assay systems (such as are described in U.S. Pat. Nos. 4,740,459 and 5,955,604). In particular, the fluorogenic substrates of the invention enable the detection of β-lactamase activity in a wide variety of biologically important environments, such as human blood serum, the cytoplasm of cells and intracellular compartments; this facilitates the measurement of periplasmic or secreted β-lactamase.

Further, the expression of any target protein can be detected by fusing a gene encoding the target protein to a β-lactamase gene, which can be localized by immunostaining and fluorescence or electron microscopy. For example, . β-lactamase fusion proteins may be detected in the lumen of organelles through the use of the substrates of the invention; only subcellular compartments containing the fusion protein fluoresce at a wavelength characteristic of the cleaved substrate, whereas all others fluoresce at a wavelength characteristic of the intact molecule.

Both the intact and cleaved substrate are well retained in cells without the use of special measures, such as chilling. The color change (even in individual small mammalian cells) is visible through a fluorescence microscope using normal color vision or photographic film; the fluorescence signal may be quantified and further enhanced by conventional digital image processing techniques. Moreover, because gene activation is detected not by a change in a single intensity but rather by a color change or a change in the ratio between two intensities at different wavelengths, the assays of the present invention are relatively immune to many artifacts such as variable leakiness of cells, quantity of substrate, illumination intensity, absolute sensitivity of detection and bleaching of the dyes.

A variety of substrates (e.g., the compounds above and in Table 1) have been prepared and their emission spectra can be obtained before and after β-lactamase cleavage. These substrates allow for β-lactamase detection primarily in vitro, as they bind strongly to serum and cellular proteins. Due to their hydrophobic nature, the fluorophores stack; this leads to a loss of fluorescence in the intact substrate. β-lactamase cleaves the substrates and relieves the stacking, allowing for fluorescence.

The substrates of this invention make it feasible to use β-lactamase as a reporter gene to monitor the expression from a set of expression control sequences. In one aspect, this invention provides methods for monitoring gene expression from a set of expression control sequences by using β-lactamase as a reporter gene. A cell is provided that has been transfected with a recombinant nucleic acid molecule comprising the expression control sequences operably linked to nucleic acid sequences coding for the expression of β-lactamase.

As used herein, the term "nucleic acid molecule" includes both DNA and RNA molecules. It will be understood that when a nucleic acid molecule is said to have a DNA sequence, this also includes RNA molecules having the corresponding RNA sequence in which "U" replaces "T." The term "recombinant nucleic acid molecule" refers to a nucleic acid molecule which is not naturally occurring, and which comprises two nucleotide sequences which are not naturally joined together. Recombinant nucleic acid molecules are produced by artificial combination, e.g., genetic engineering techniques or chemical synthesis.

Nucleic acids encoding β-lactamases can be obtained by methods known in the art, for example, by polymerase chain reaction of cDNA using primers based on the DNA sequence known in the art and disclosed in U.S. Pat. No. 5,955,604, which is incorporated herein by reference). PCR methods are described in, for example, U.S. Pat. No. 4,683,195; Mullis et al. (1987) Cold Spring Harbor Symp. Quant. Biol. 51:263; and Erlich, ed., PCR Technology, (Stockton Press, N.Y., 1989).

The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., (most recent Supplement)).

Nucleic acids used to transfect cells with sequences coding for expression of the polypeptide of interest generally will be in the form of an expression vector including expression control sequences operatively linked to a nucleotide sequence coding for expression of the polypeptide. As used, the term nucleotide sequence "coding for expression of" a polypeptide refers to a sequence that, upon transcription and translation of mRNA, produces the polypeptide. As any person skilled in the are recognizes, this includes all degenerate nucleic acid sequences encoding the same amino acid sequence. This can include sequences containing, e.g., introns. As used herein, the term "expression control sequences" refers to nucleic acid sequences that regulate the expression of a nucleic acid sequence to which it is operatively linked. Expression control sequences are "operatively linked" to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The recombinant nucleic acid used to transfect the cell contains expression control sequences operably linked to a nucleotide sequence encoding a β-lactamase. The β-lactamase encoded can be any known to the art or described herein.

This invention provides novel recombinant nucleic acid molecules including expression control sequences adapted for function in a non-mammalian eukaryotic cell operably linked to a nucleotide sequence coding for the expression of a cytosolic β-lactamase. As used herein, "cytosolic β-lactamase" refers to a β-lactamase that lacks amino acid sequences for secretion from the cell membrane, e.g., the signal sequence.

It is further preferable that the ribosome binding site and nucleotide sequence coding for expression of β-lactamase contain sequences preferred by mammalian cells. Such sequences improve expression of β-lactamase in mammalian cells. Preferred sequences for expression in mammalian cells are described in, for example, Kozak, M., J. Cell Biol. 108.

When used in mammalian cells, the expression control sequences are adapted for function in mammalian cells. The method of this invention is useful to testing expression from any desired set of expression control sequences. In particular, this invention is useful for testing expression from inducible expression control sequences. As used herein, "inducible expression control sequences" refers to expression control sequences which respond to biochemical signals either by increasing or decreasing the expression of sequences to which they are operably linked. For example, in the case of genes induced by steroid hormones, the expression control sequences includes hormone response elements. The binding of a steroid hormone receptor to the response element induces transcription of the gene operably linked to these expression control sequences. Expression control sequences for many genes and for inducible genes, in particular, have been isolated and are well known in the art. The invention also is useful with constitutively active expression control sequences.

The transfected cell is incubated under conditions to be tested for expression of β-lactamase from the expression control sequences. The cell or an extract of the cell is contacted with a β-lactamase substrate of the invention under selected test conditions and for a period of time to allow catalysis of the substrate by any β-lactamase expressed. Then the donor moiety from this sample is excited with appropriate ultraviolet or visible wavelengths. The degree of fluorescence resonance energy transfer in the sample is measured.

If the cell did not express β-lactamase, very little of the substrate will have been cleaved, the efficiency of FRET in the cell will be high, and the fluorescence characteristics of the cell or sample from it will reflect this efficiency. If the cell expressed a large amount of β-lactamase, most of the substrate will be cleaved. In this case, the efficiency of FRET is low, reflecting a large amount or high efficiency of the cleavage enzyme relative to the rate of synthesis of the tandem fluorescent protein construct. In one aspect, this method can be used to compare mutant cells to identify which ones possess greater or less enzymatic activity. Such cells can be sorted by a fluorescent cell sorter based on fluorescence.

Also, as will be apparent to those working in the field of using reporter gene cell-based assays for screening samples or pools of samples (such as compounds (combinatorial or synthetic), natural product extracts, or marine animal extracts) to identify potential drug candidates which act as agonists, inverse agonists or antagonists of cellular signaling or activation, the combination of cells (preferably mammalian) genetically engineered to express β-lactamase under the control of different regulatory elements/promoters and the use of the novel β-lactamase substrate compounds of the present invention will provide distinct advantages over known reporter genes (including, but not limited to, chloramphenicol acetyl transferase, firefly luciferase, bacterial luciferase, vargula luciferase, aequorin, β-galactosidase, alkaline phosphatase) and their requisite substrates.

By the choice of appropriate regulatory elements and promoters to control expression of β-lactamase, assays can be constructed to detect or measure the ability of test substances to evoke or inhibit functional responses of intracellular hormone receptors. These include expression control sequences responsive to inducible by mineralcorticosteroids, including dexamethasone (J. Steroid Biochem. Molec. Biol. Vol. 49, No. 1 1994, pp.31), gluococorticoid, and thyroid hormone receptors (as described in U.S. Pat. No. 5,071,773). Additional such intracellular receptors include retinoids, vitamin D3 and vitamin A (Leukemia vol 8, Suppl. 3, 1994 ppS1-S10; Nature Vol. 374, 1995, p.118-119; Seminars in Cell Biol., Vol. 5, 1994, p.95-103). Specificity would be enabled by use of the appropriate promoter/enhancer element. Additionally, by choice of other regulatory elements or specific promoters, drugs which influence expression of specific genes can be identified. Such drugs could act on specific signaling molecules such as kinases, transcription factors, or molecules such signal transducers and activators of transcription (Science Vol. 264, 1994, p.1415-1421; Mol. Cell Biol., Vol. 16, 1996, p.369-375). Specific microbial or viral promoters which are potential drug targets can also be assayed in such test systems.

Also by the choice of promoters such as c-fos or c-jun (U.S. Pat. No. 5,436,128; Proc. Natl. Acad. Sci. Vol. 88, 1991, pp. 5665-5669) or promoter constructs containing regulatory elements responsive to second messengers (Oncoqene, 6:745-751 (1991)) (including cyclic AMP-responsive elements, phorbol ester response element (responsive to protein kinase C activation), serum response element (responsive to protein kinase C-dependent and independent pathways) and Nuclear Factor of Activated T-cells response element (responsive to calcium) to control expression of β-lactamase, assays can be constructed to detect or measure substances or mixtures of substances that modulate cell-surface receptors including, but not limited to, the following classes: receptors of the cytokine superfamily such as erthyropoietin, growth hormone, interferons, and interleukins (other than IL-8) and colony-stimulating factors; G-protein coupled receptors (U.S. Pat. No. 5,436,128) for hormones, such as calcitonin, epinephrine or gastrin, pancrine or autocrine mediators, such as stomatostatin or prostaglandins, and neurotransmitters such as norepinephrine, dopamine, serotonin or acetylcholine; tyrosine kinase receptors such as insulin growth factor, nerve growth factor (U.S. Pat. No. 5,436,128). Furthermore, assays can be constructed to identify substances that modulate the activity of voltage-gated or ligand-gated ion channels, modulation of which alters the cellular concentration of second messengers, particularly calcium (U.S. Pat. No. 5,436,128). Assays can be constructed using cells that intrinsically express the promoter, receptor or ion channel of interest or into which the appropriate protein has been genetically engineered.

The expression control sequences also can be those responsive to substances that modulate cell-surface receptors or that modulate intra-cellular receptors.

To measure whether a substance or mixture of substances activates extracellular or intracellular receptors or other cellular responses, cells containing β-lactamase controlled by a desired promoter/enhancer element are incubated with test substance(s), substrate then added, and after a certain period of time the fluorescence signal is measured at either one or two excitation-emission pairs appropriate to the chosen compound of the invention (e.g. compound CCF2 with wavelength pairs of near 405 nm and near 450 nm and near 405 and near 510 nm). This fluorescent result is compared to control samples which have had no drug treatment and, when feasible, control samples with a known inhibitor and a known activator. The effect of any active drugs is then determined using the ratio of the fluorescence signal found in test wells to the signals found in wells with no drug treatment. Assays are performed in wells in a microtiter plate containing 96 or more wells or in an assay system with no compartments such as a gel matrix or moist membrane environment. Detection could be done for example by microtiter plate fluorimeters, e.g. Millipore Cytofluor, or imaging devices capable of analyzing one or more wells or one or more assay points in a certain surface area, e.g. as supplied by Astromed. The ability to retain the substrate in the cytoplasm of living cells is advantageous as it can allow a reduction in signal interference from coloured or quenching substances in the assay medium. Furthermore, the fluorescent signal from the compounds of this invention, such as CCF2, can be readily detected in single cells and thus allowing assay miniaturization and an increased number of tests per surface area. Miniaturized assays also further increase the throughput of an imaging detection system as there are more samples within the imaging field.

The assay systems of the present invention further provide an advantageous and rapid method of isolation and clonal selection of stably transfected cell lines containing reporter genes and having the desired properties which the transfection was intended to confer, e.g. fluorescent signal response after activation of a transfected receptor with a high signal-to-noise ratio of at least 10:1 from a high proportion of isolated cells. Current procedures for clonal selection of satisfactorily transfected, genetically engineered cells from the population initial transfected with the vectors of interest, are done mainly by manual means and involve several rounds of microscopic analyses, selecting the visually preferred clone, isolation of the clone by manual pipetting stages and prolonged cellular cultivations. This procedure is laborious and time-consuming; it may require several months to generate a clone useful for assays suited to drug screening. Moreover, it is difficult to manually select and maintain more than a few hundred clones. Using the assays of this present invention, the desired signal from cellular β-lactamase reporter system can be maintained within living and viable cells. Thus, one can rapidly select, from the population of initially transfected cells, those few living cells with the best fluorescent signal using automated instruments such as a fluorescent-activated cell sorter, e.g. the Becton Dickinson FACS Vantage. The selected cells are then collected for cultivation and propagation to produce a clonal cell line with the desired properties for assays and drug screening.

In addition, the presence (for example, in human serum, pus or urine) of bacteria resistant to β-lactam antibiotics can be readily detected using the substrates of the present invention. Only in the presence of an active β-lactamase is there a change in the fluorescence spectrum from that of the intact molecule to one characteristic of the cleavage product. The substrates of the present invention are superior to prior art chromogenic substrates Nitrocephin and PADAC, in that the inventive substrates are stable to human serum. The novel substrates are also more sensitive than the chromogenic substrate CENTA, because they experience a much smaller optical background signal from human serum and a lower detection limit for fluorescence versus absorbance.

The invention may be better understood with reference to the accompanying examples, which are intended for purposes of illustration only and should not be construed as in any sense limiting the scope of the invention as defined in the claims appended hereto.

The degree of FRET or amount of fluorescence can be determined by any spectral or fluorescence lifetime characteristic of the excited construct, for example, by determining the intensity of the fluorescent signal from the donor, the intensity of fluorescent signal from the acceptor or quencher, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in the degree of fluorescence or FRET are determined, for example, as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The excitation state lifetime of the donor moiety is, likewise, independent of the absolute amount of substrate, excitation intensity, or turbidity or other background absorbances. Its measurement requires equipment with nanosecond time resolution, except in the special case of lanthanide complexes in which case microsecond to millisecond resolution is sufficient.

Fluorescence in a sample is measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., Principles of Fluorescence Spectroscopy, New York:Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp.

219-243; Turro, N.J., Modern Molecular Photochemistry, Menlo Park: Benjamin/Cummings Publishing Col, Inc. (1978), pp. 296-361.

The Figures and figure legends attached hereto depict assays based upon the methods and substrates identified above.

All publications and patent documents cited in this application are incorporated by reference in their entirety for all purposes to the same extent as if each individual publication or patent document were so individually denoted.

The present invention provides novel substrates for β-lactamase, β-lactamases and methods for their use. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

What is claimed is:

1. A compound having the general formula:

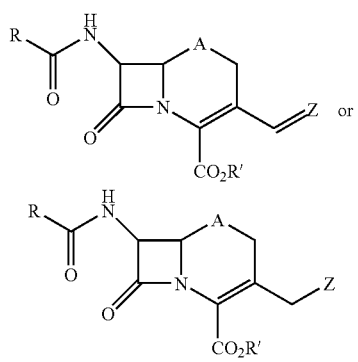

or in which R is a benzyl, 2-thienylmethyl, or cyanomethyl group;

R' is selected from the group consisting of H, physiologically acceptable salt or metal, the ammonium cation, —CHR$_2$OCOC(CH$_3$)$_3$, in which $R_2$ is selected from the group consisting of H, lower alkyl;

deltabutyrolactonyl, methoxycarbonyloxymethyl, phenyl, methylsulphinylmethyl, β-morpholinoethyl, dialkylaminoethyl, and dialkylaminocarbonyloxymethyl;

A is selected from the group consisting of O, SO, and SO$_2$; and

Z is selected from:

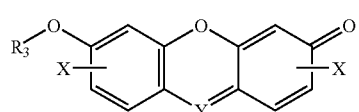

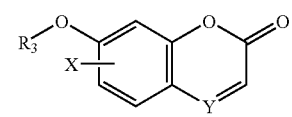

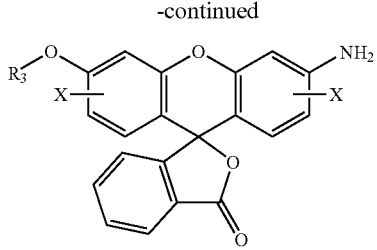

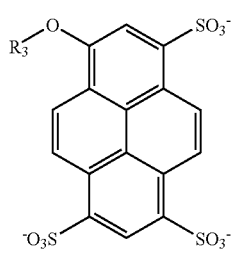

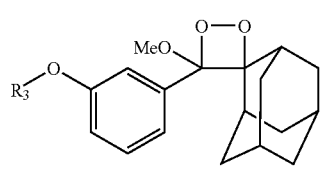

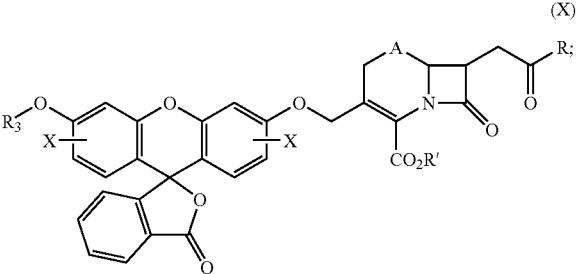

and

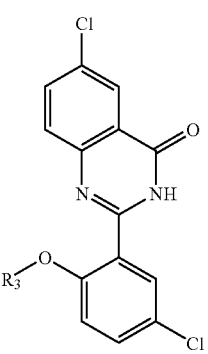

wherein $R_3$ is a linker;

X is H, F, Cl, Br, or CO$_2$R'; and

Y is N, CH, C—CN, or C—CF$_3$.

2. A compound comprising the structure:
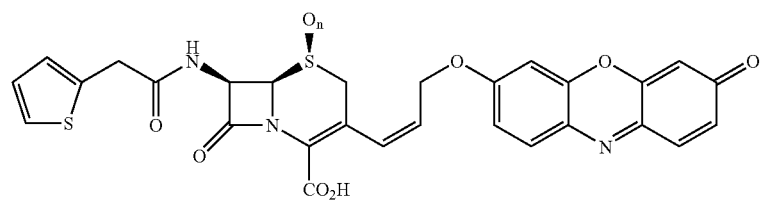
wherein n is 0, 1, or 2.
* * * * *